United States Patent [19]

Biesel

[11] Patent Number: 5,298,171
[45] Date of Patent: Mar. 29, 1994

[54] METHOD AND APPARATUS FOR SEPARATION OF BLOOD INTO ITS COMPONENTS

[75] Inventor: Wolfgang Biesel, Ottweiler, Fed. Rep. of Germany

[73] Assignee: Fresenius AG, Fed. Rep. of Germany

[21] Appl. No.: 927,101

[22] Filed: Aug. 7, 1992

[30] Foreign Application Priority Data

Aug. 9, 1991 [DE] Fed. Rep. of Germany ....... 4126341

[51] Int. Cl.$^5$ ........................ B01D 21/30; B01D 21/26
[52] U.S. Cl. ...................................... 210/739; 210/87; 210/97; 210/103; 210/143; 210/321.65; 210/360.1; 494/37; 604/5
[58] Field of Search ................... 210/87, 103, 97, 96.1, 210/143, 195.2, 321.65, 321.67, 321.68, 360.1, 512.1, 782, 739, 789, 929; 422/72, 45, 46, 48, 228; 604/4, 5, 6; 494/3, 10, 11, 37, 84

[56] References Cited

U.S. PATENT DOCUMENTS

| | | | |
|---|---|---|---|
| 3,957,197 | 5/1976 | Sartory et al. | 494/10 |
| 4,185,629 | 1/1980 | Cullis et al. | 604/6 |
| 4,964,847 | 10/1990 | Prince | 604/4 |
| 4,968,295 | 11/1990 | Neumann | 604/4 |

Primary Examiner—Robert A. Dawson
Assistant Examiner—Sun Uk Kim
Attorney, Agent, or Firm—Robbins, Berliner & Carson

[57] ABSTRACT

In a separation device for separation of blood into its components, the hematocrit value of the blood to be separated plays a significant role relative to the sedimentation of cellular blood components. Since in blood processing, particularly in the intraoperative area, significant fluctuations of the incoming hematocrit value may occur, for example, due to infused volume expander, irrigation solutions, anticoagulant additives, etc., it is useful for maintenance of a blood separation working with constant values, particularly a constant hematocrit value of the erythrocyte fraction, to take the preset hematocrit value of the blood to be separated into account. According to the invention, the rate of blood flow through the separation device is automatically adjusted as a function of the hematocrit value of the incoming blood.

16 Claims, 4 Drawing Sheets

METHOD AND APPARATUS FOR SEPARATION OF BLOOD INTO ITS COMPONENTS

BACKGROUND OF THE INVENTION

The invention concerns a separation device for separation of blood into its components within the framework of in-vivo blood processing, with a separator which has a intake line with a pump whose flow can be adjusted to supply the blood to be separated and discharge lines for the separated output of at least the erythrocyte fraction and the cell-poor plasma, as well as a return line via which at least one component can be returned to the donor/patient, and with a control arrangement to which a signal representing the hematocrit value of the incoming blood (hematocrit signal) is sent.

Such a separation device, which is used in particular during intraoperative blood processing, is known from U.S. Pat. No. 3,957,197. In the known case, the hematocrit signal is connected to a regulating step with which the hematocrit value of the whole blood (proportion of erythrocytes to the volume of the peripheral blood in vol.-%) is kept at a constant value. For this the hematocrit value of the whole blood is measured in the intake line (actual value) and compared to a desired value. If the hematocrit value measured is higher than the desired value, it is adjusted to the preset value by addition into the intake of a separated fraction from the appropriate discharge lines via a precision dosing pump. Thus, the relationship of plasma flow to erythrocyte flow can be adjusted to a constant defined value and an improvement in the efficiency of the separation device with regard to cell collection in treatment of relatively large amounts of blood can thus be obtained.

Devices with improved efficiency in blood collection and treatment of larger amounts of blood are also presented in DE 34 10 286 A1 (identical to EP 0 155 684 A2). DE 34 10 286 A1 describes a device whereby the hematocrit of whole blood delivered to a centrifuge is adjusted in the desired low range (e.g., 25%) by means of plasma return, and whereby the centrifuge accomplishes optimum separation efficiency. The centrifuge separates the blood the most rapidly at an input value of 25% erythrocytes in the whole blood and with constant input flow and constant speed; the final value of the hematocrit of the cell concentrate, i.e., the erythrocyte fraction (e.g., 70%) is obtained the most rapidly. For this reason, plasma obtained through centrifuging is added and the blood thus thinned.

An analogous prior art device with control of the hematocrit value of the whole blood delivered at a constant value was disclosed in the article by B. J. Van Wie and S. S. Sofer: "The effect of recycle on the continuous centrifugal processing of blood cells", The International Journal of Artificial Organs, Vol. 8, No. 1, 1985, pp. 43–48.

However, in certain medical applications, in particular in intraoperative blood processing, one must assume widely scattered (i.e., extremely varied) high hematocrit values for the whole blood supplied to a separation device, which values cannot be influenced by control technology. The known devices cannot be used in those cases. However, the hematocrit value of the incoming blood plays a significant role relative to the sedimentation of cellular blood components in a centrifuge, since sedimentation is a function of the hematocrit value in addition to the size, density, and shape of the blood cells. Consequently, incoming blood with different hematocrit values is separated into cell fractions of differing concentrations if it is processed for the same length of time in a centrifuge. This relationship between the hematocrit value of the blood (=Hk blood in %) and the hematocrit value of the erythrocyte fraction (HkEk in %) with a constant blood flow of 120 ml/min is depicted in FIG. 1. The HkEK decreases as Hk blood increases.

The relationships are similar with other separation devices, in particular filtration systems which can also be used.

The dependency depicted in FIG. 1 is without particular significance in those typical cases wherein adequate processing periods in the centrifuges can be implemented and wherein possibly even relatively poor separation efficiency is acceptable. Furthermore, on average the incoming hematocrit value of the donor blood has only slight fluctuations, so that the associated effects are also negligible in such cases.

However, the situation is different particularly in the area of intraoperative autotransfusion, in particular during plasma separation and irrigation processes. There, the hematocrit value plays a very critical role. Intraoperative blood suctioned in the operative field and temporarily held in a collection container has quite variable hematocrit values depending on the type of operation, the hematocrit value of the patient, the amount of irrigation solution used in the operative field, the amount of volume expander infused, patient blood loss, the amount of anticoagulant added, or the amount of fluid flowing in, for example from the tissue. These are in the range from ten to forty percent and can vary arbitrarily during an operation. In contrast, the normal values are forty-six percent by volume for men and forty for women. The processing methods currently used do not take these fluctuations in the hematocrit value into account and usually operate with constant, preset rates of delivery of blood into the centrifuge. This leads to the following consequences:

1. The hematocrit value of the erythrocyte concentrate produced is subject to large fluctuations.
2. The plasma washout rate, which is defined by the volume relationship of the residual plasma to be washed out remaining in the cell concentrate to the irrigation solution added, is subject to significant fluctuations.
3. The sedimentation capacity of the separation device cannot be optimally utilized.

Furthermore, a constant hematocrit value of the erythrocyte concentrate produced is imperative for the exact documentation of the retransfused erythrocyte quantity by the retransfused erythrocyte concentrate volume. It is desirable to work with the highest possible blood processing speed and to work with a constant washout rate.

The object of the invention is to improve the separation device described in the introduction such that despite the widely fluctuating hematocrit value of the incoming blood a constant hematocrit value of the prepared cell concentrate can be obtained. Additional objectives are a constant washout rate and optimum utilization of the sedimentation performance of the separation device used to optimize blood throughput.

SUMMARY OF THE INVENTION

In accordance with the present invention, a separation device is provided wherein the control arrangement has a regulating stage with a preset transmission function whose input supplies the hematocrit signal and whose output is linked to the pump (16) in the intake line and the transmission function is defined such that, depending on the magnitude of the hematocrit signal, an adjustment signal can be derived at the output of the regulating step which adjusts the flow of the blood through the pump (16) such that the hematocrit value of the erythrocyte fraction returned has a constant value.

The invention thus offers the advantages that despite a broadly scattered hematocrit value in the incoming blood—in the area of intraoperative autotransfusion, fluctuations in the range of approximately 10 to 40% occur—a constant hematocrit value of the cell concentrate can however be achieved by controlling the blood flow and the associated varied separation. In this process, the separation time is optimally short, i.e., the efficiency of the system is optimized with regard to the process capability.

BRIEF DESCRIPTION OF THE DRAWINGS

In the following, the invention is described with reference to exemplary embodiments which are depicted in the drawings, in which.

DETAILED DESCRIPTION OF THE INVENTION

The respective exemplary embodiments refer to separators in the form of a blood centrifuge. However, other separators, e.g., filtration systems, which separate the blood cells from the fluid may be used.

Whenever the term blood is used in the following, it should also be understood to refer generally to suspensions containing blood cells, i.e., blood/solution mixtures as well.

Figure 1:
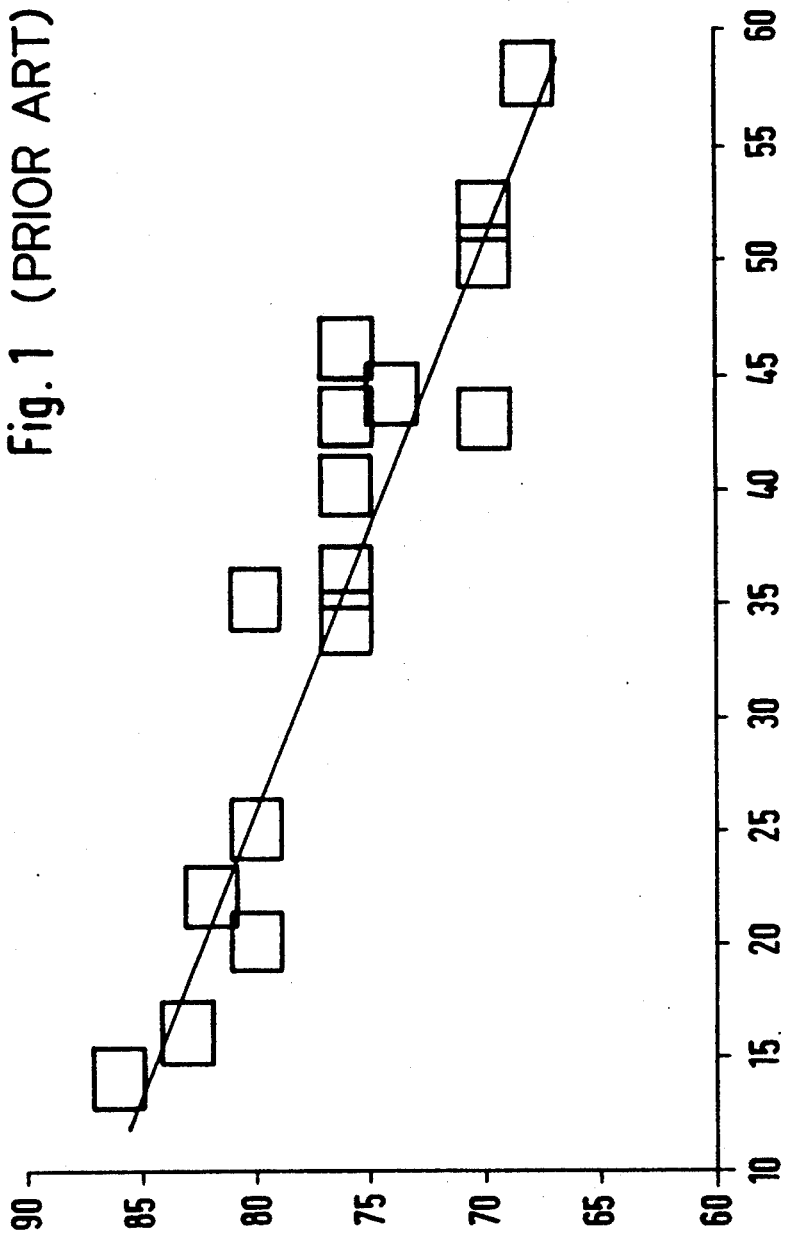
FIG. 1 is a representation of the dependency of the hematocrit value Hk of the erythrocyte fraction Ek on the Hk of the incoming blood with constant flow.

FIG. 1 depicts the relationship between the hematocrit value Hk of the blood to be separated and that of the cell concentrate Ek with the preset blood flow $V_B$ of 120 ml/min. It is quite obvious that blood with a different hematocrit value with the same amount of time in a centrifuge, i.e., with constant delivery speed, is separated into cell fractions with varying concentrations. The higher the Hk of the blood, the lower the HkEk. FIG. 1 thus depicts the situation known from the prior art.

Figure 2:
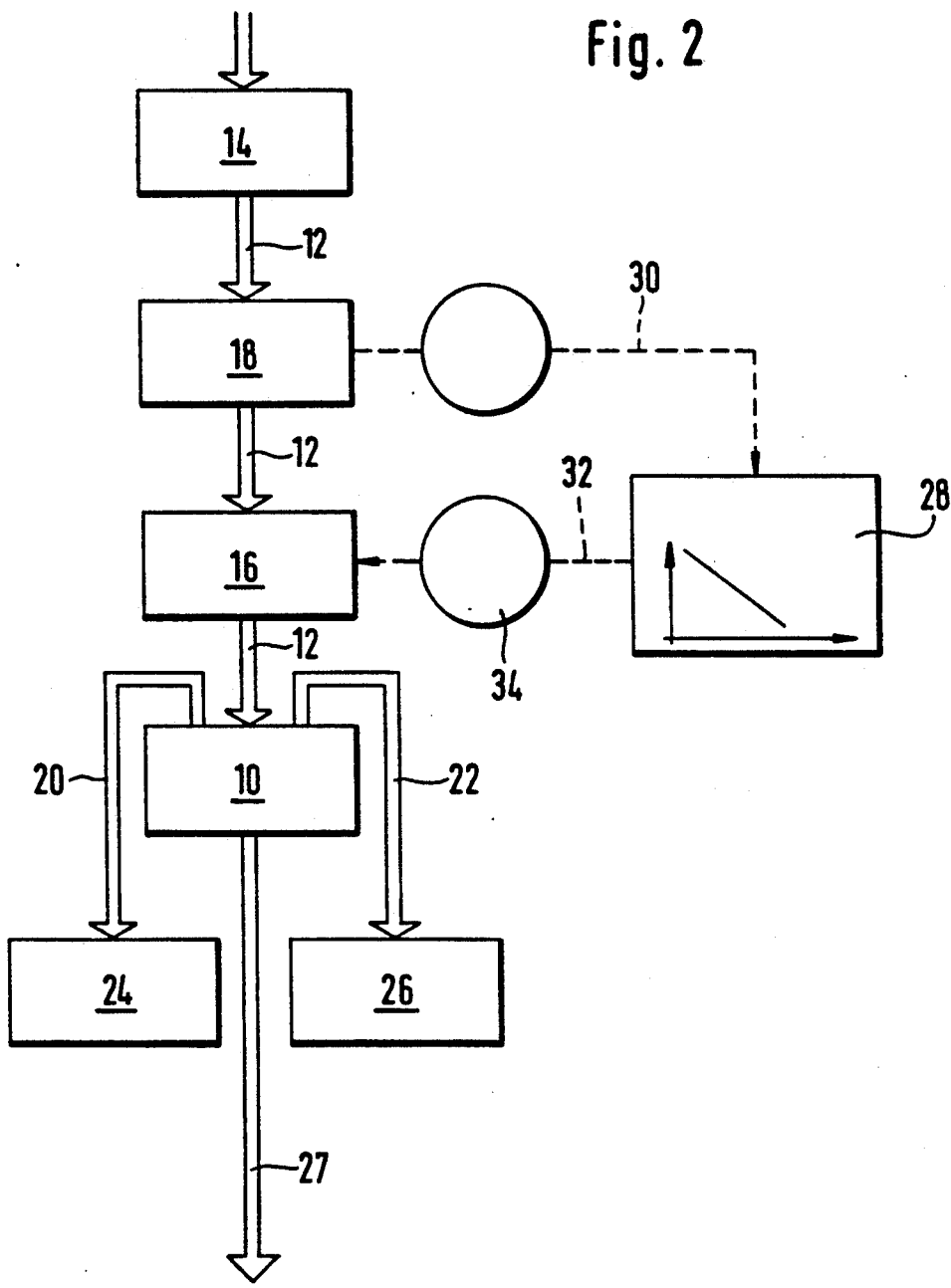
FIG. 2 is a schematic block diagram of a separation device pursuant to the invention.

FIG. 2 depicts a centrifuge 10 as a separator, which has an intake line 12 to supply the blood found in a blood source 14 to be separated or processed. Connected in this intake line are a blood pump 16 with an adjustable speed which varies the flow of blood and a hematocrit sensor 18 upstream from it. With the sensor 18, the hematocrit value of the incoming blood $Hk_B$ is determined using known methods, e.g., photoelectrically or with a conductivity measurement. The other components 10 through 16 are known assemblies so that a more detail description thereof is superfluous.

The centrifuge 10 also has discharge lines 20 and 22 for the separated output of the blood components, whereby in FIG. 2 only two components, the erythrocyte fraction and the cell-poor plasma are collected in their respective containers 24 and 26. For simplicity and clarity, in FIG. 2 all additional components of the separator system are omitted, e.g., the in-vivo blood extraction and also the usual pumps in the discharge lines. The cell concentrate return line to the patient/donor is labeled 27 in FIG. 2.

FIG. 2 also depicts a regulating stage 28 to whose input the signal representing the hematocrit value of the incoming blood, the hematocrit signal $Hk_B$, is sent via the line 30 and whose output is linked via the line 32 with the adjustment device 34 for the pump speed of the blood pump 16 and thus for the blood flow $\dot{V}_B$. The regulating stage 28 may be constructed from known analog control circuits. It is preferably made up of a microprocessor. The transmission function of the regulating stage 28 is defined such that an adjustment signal $\dot{V}_B$ can be derived as a function of the magnitude of the input signal $Hk_B$, which adjusts the flow rate of the blood such that the hematocrit value has a constant value considering the typical time delay for the respective separation chamber, here the erythrocyte fraction returned to the patient. The presetting of the transmission function $\dot{V}_B = f(Hk_B)$ in the regulating step 28 is performed using diagrams of characteristics determined empirically or by computer.

Figure 3:
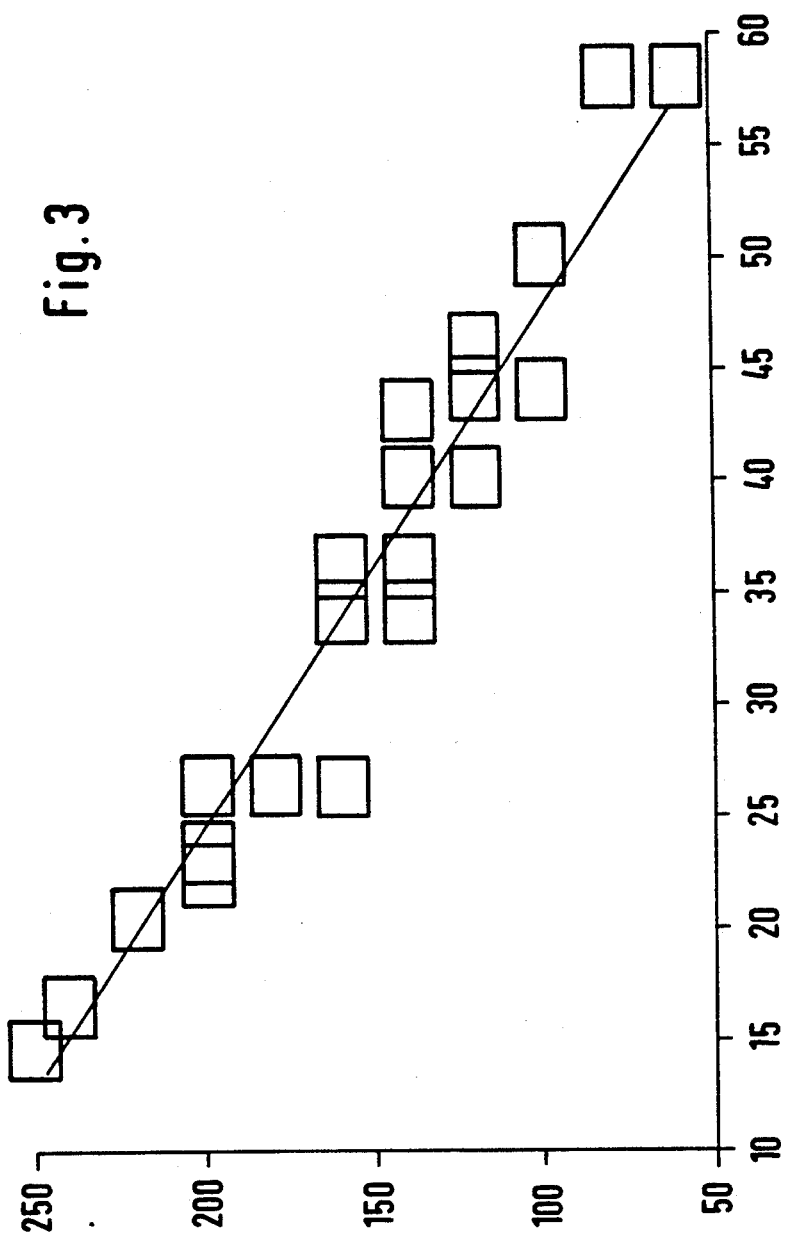
FIG. 3 is a representation of the dependency of the hematocrit value of the blood to be separated on the blood flow with a constant hematocrit value of the cell fraction.

FIG. 3 depicts an example of such a diagram of characteristics which represents the relationship between the incoming hematocrit value $Hk_B$ and blood flow $\dot{V}_B$ with a constant hematocrit of the erythrocyte fraction HkEk=75%. For each $Hk_B$ measured there is a value $\dot{V}_B$ at which the preset HkEk is achieved. This process according to FIG. 3 with continuous measurement of the hematocrit value $Hk_B$ is particularly suited for use with centrifuges with continuous and discontinuous modes of operation (blood flow centrifuge or batch processing).

Figure 4:
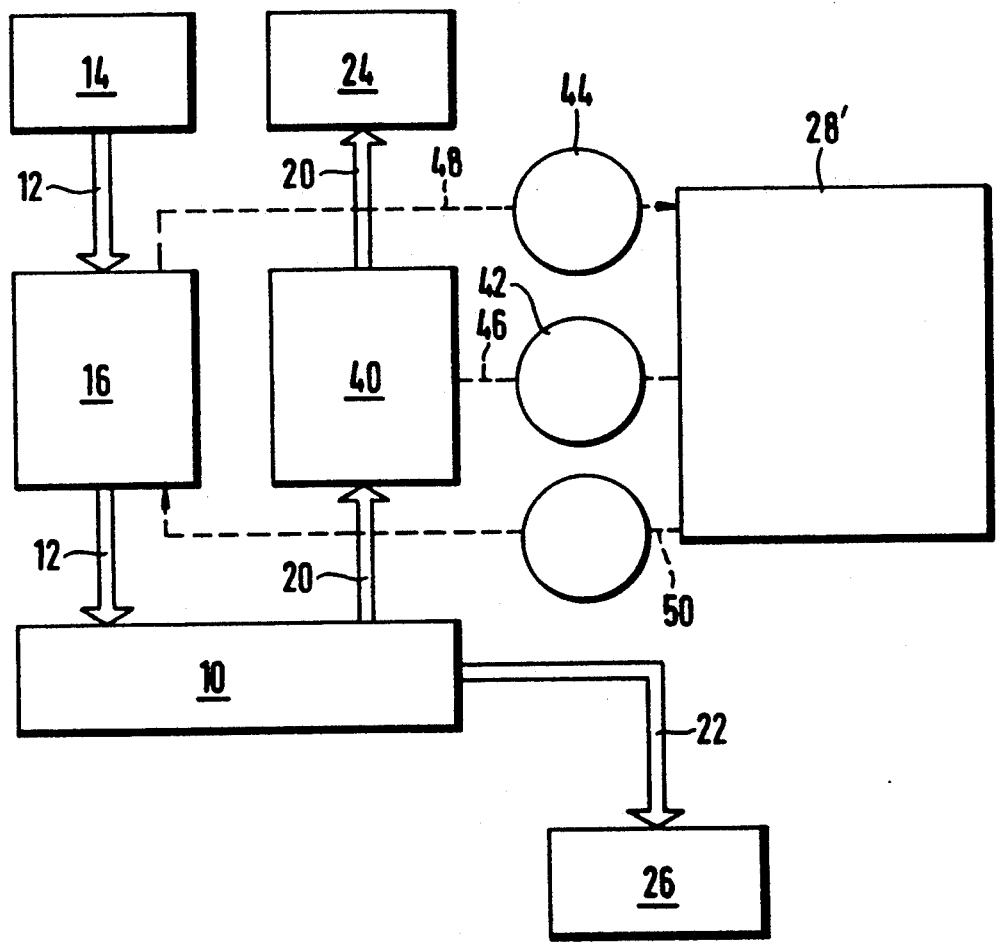
FIG. 4 is a block diagram of an additional exemplary embodiment of a separation device pursuant to the invention.

In the device according to FIG. 2, the hematocrit value is measured directly and continuously. FIG. 4 depicts an alternative embodiment of a device according to the invention whereby the hematocrit determination occurs indirectly. Such a method is particularly applicable with blood flow centrifuges with systems for balancing the component flows into and out of the separation chamber (blood, plasma, irrigation solution, erythrocyte concentrate). Here the hematocrit determination takes place by computer approximation from the blood flow into the separation chamber and from the erythrocyte concentrate flow or plasma flow from the separation chamber using one of the two following formulas.

$$Hk_B = \frac{V_{EK}}{V_B} \cdot K \quad \text{(a)}$$

or $$Hk_B = \frac{V_B - V_{PLS}}{V_B} \cdot K \quad \text{(b)}$$

$Hk_B$ = Hk of the blood

K = constant
$\dot{V}_{EK}$ = erythrocyte concentrate flow
$\dot{V}_B$ = blood flow
$\dot{V}_{PLS}$ = plasma flow The constant K corresponds to the desired hematocrit value typical for the diagram of characteristics of the erythrocyte concentrate pursuant to FIG. 3, e.g., a value of 75% (target hematocrit).

Alternative (a) is depicted in FIG. 4. All parts of the device according to FIG. 4 which correspond to those of FIG. 2 have the same reference numbers. Also depicted are the pump 40 in the discharge line 20 of the erythrocyte fraction, the sensor 42 to obtain the erythrocyte concentrate flow reading (actual $\dot{V}_{EK}$), and the sensor 44 to obtain the blood flow reading (actual $\dot{V}_B$) in the centrifuge 10. Here, the sensor 42 is connected with the Ek pump 40 via the line 46, and the sensor 44 is connected with the blood pump 16 via the line 48.

Compared to the regulating stage 28 of FIG. 2, the regulating stage 28' is expanded. The hematocrit signal $Hk_B$ is no longer applied directly to the regulating stage 28', but rather is first virtually formed in an additional upstream step. If the regulating stage 28' consists of a microprocessor, the step differences are no longer designed as hardware, but can be found in the program. The outlines of stages 28 in FIG. 2 and stages 28' in FIG. 4 should thus be considered as functions and not as walls of the housings.

Adjustment of the blood flow to the blood pump 16 starts from a preset value $V_B$, which assures a hematocrit value of the erythrocyte concentrate of 75±10%, for example, over the entire hematocrit range in the incoming blood. Here the output of the regulation stage 28' is linked via a line 50 with the input of the blood pump 16, to which the value $V_B$SOLL (desired $V_B$) to be adjusted is connected. After setting a state of equilibrium, the $V_{EK}$ is determined or the hematocrit value of the incoming blood is calculated and the blood flow is adjusted accordingly. Such a state of equilibrium is characterized, for example, by a relationship of blood flow and erythrocyte concentrate flow or plasma flow corresponding to the hematocrit of the incoming blood and thus by a constant filled state of the centrifuge. The deviation between the hematocrit value calculated and the actual hematocrit value depends on the difference between the blood flow actually set $V_B$IST and the blood flow (VBlut) to be adjusted according to FIG. 3. Through progressive adaptation of the blood flow according to the hematocrit value determined, the difference between the preset blood flow and the blood flow to be set and thus also the error in the calculation of the hematocrit is reduced. This can be seen from the following example of hematocrit-based blood flow adjustment.

Limit conditions:
desired hematocrit of the erythrocyte concentrate $Hk_{EK}$ = 75%
maximum blood flow $V_B$ = 120 ml/min, which also permits a $Hk_{EK}$ greater than 70% in the higher $Hk_B$ range
blood to be processed with $Hk_B$ = 20%
separation chamber PL1 at 2,000 rpm Adjustment process (1st computational example):
Starting condition: preset blood flow $V_B$ = 120 ml/min leads to a concentrate flow $\dot{V}_{EK}$ of 29 ml/min with $Hk_{EK}$ = 83%;
1st adjustment step:

$$\text{calculated } Hk_B = \frac{29}{120} \cdot 75 = 18.2\%;$$

Setting of $\dot{V}_B$ (18.2) according to FIG. 3 = 220 ml/min → concentrate flow $\dot{V}_{EK}$ = 60 ml/min with $Hk_{EK}$ = 72%

2nd adjustment step:

$$\text{newly calculated } Hk_B = \frac{60}{220} \cdot 75 = 20.5\%;$$

Setting of $\dot{V}_B$ (20.5) according to FIG. 3 = 200 ml/min → concentrate flow $\dot{V}_{EK}$ = 56 ml/min with $Hk_{EK}$ = 75%.

Thus, with the control according to the invention per FIG. 4, automatic setting of the desired $Hk_{EK}$ of 75% occurs with maximum concentrate flow. The unregulated system remains under the conditions identified as starting conditions and produces erythrocyte concentration of $Hk_{EK}$ = 83% with a concentrate flow of 29 ml/min. In place of the hematocrit-based blood flow setting described, a setting of the blood flow based on the erythrocyte concentrate (EK) flow is also possible, since according to the equation $\dot{V}_{EK} = f(Hk_B)$ the hematocrit can be represented by the erythrocyte concentrate flow $V_{EK}$. The following calculation example illustrates the EK-flow-based blood flow setting:

2nd computational example:

Starting condition: Desired $EK$ flow = 56 ml/min ($\dot{V}_{EK}SOLL$)

($Hk_{EK}$ = 75%)

Preset blood flow $\dot{V}_B$ = 120 ml/min yields a $\dot{V}_{EK}$IST of 29 ml/min ($Hk_{EK}$·83%)

1st adjustment step:

$$\frac{\dot{V}_{EK}SOLL}{\dot{V}_{EK}IST} = \frac{56 \text{ ml/min}}{29 \text{ ml/min}} = 1.93$$

Setting of $\dot{V}_B$SOLL = $\dot{V}_B$IST·1.93 = 120 ml/min·1.93 ≈ 232 ml/min

2nd adjustment step:

$\dot{V}_B$ = 232 ml/min yields a $\dot{V}_{EK}$IST = 65 ml/min ($Hk_{EK}$ = 70%)

$$\frac{\dot{V}_{EK}SOLL}{\dot{V}_{EK}IST} = \frac{56 \text{ ml/min}}{65 \text{ ml/min}} = 0.86$$

Setting of $\dot{V}_B$SOLL = $\dot{V}_B$IST · 0.86
 = 232 ml/min · 0.86 ≈ 200 ml/min ($\dot{V}_B$SOLL) of 200 ml/min yields a $\dot{V}_{EK}$ = 56 ml/min ($Hk_{EK}$ = 75%)

In the following table, the values $\dot{V}_{EK}$ and $Hk_{EK}$ for hematocrit values of the incoming blood of 10–40% in the controlled and the uncontrolled system are juxtaposed.

| | controlled | | uncontrolled | |
|---|---|---|---|---|
| $Hk_B$ % | $\dot{V}_{EK}$ ml/min | $Hk_{EK}$ % | $\dot{V}_{EK}$ ml/min | $Hk_{EK}$ % |
| 10 | 53 | 75 | 14 | 90 approx. |
| 20 | 56 | 75 | 29 | 83 |

-continued

| Hk$_B$ % | controlled | | uncontrolled | |
|---|---|---|---|---|
| | V$_{EK}$ ml/min | Hk$_{EK}$ % | V$_{EK}$ ml/min | Hk$_{EK}$ % |
| 30 | 56 | 75 | 48 | 78 |
| 40 | 54 | 75 | 64 | 73 |

The undesired broad fluctuations of the hematocrit value of the erythrocyte concentrate Hk$_{EK}$ from 73-90% are obvious in the uncontrolled case compared to the constant value of 75% in the controlled case.

The invention is not restricted to the embodiments depicted. There are, rather, a variety of variant and modification possibilities within the framework of the invention, as defined in the appended claims.

I claim:

1. Apparatus for separation of blood into its components, comprising:
    a separator having:
        an intake line with a pump for adjusting supply of the blood to be separated,
        a plurality of discharge lines for separated output of at least an erythrocyte fraction and a cell-poor plasma fraction, and
        a return line for returning at least one fraction to a donor or patient, and
    a control arrangement having:
        a regulating means including an input means for receiving a hematocrit signal representing hematocrit value of incoming blood and means with a preset transmission function for deriving, in response to the hematocrit signal, an adjustment signal and means for adjusting the pump in response to the adjustment signal such that the hematocrit value of the erythrocyte fraction returned has a constant value.

2. The apparatus according to claim 1, further comprising a sensor in the intake line for continuous measurement of the hematocrit value to provide the hematocrit signal.

3. The apparatus according to claim 1, wherein the control arrangement including the regulating means comprises a microprocessor.

4. The apparatus according to claim 1, wherein the separator is a centrifuge.

5. The apparatus according to claim 1, further comprising:
    a first sensor for deriving a signal reporting the blood flow into the separator, and
    a second sensor at the output of the separator to determine the flow of a separated fraction,
    wherein the regulating means including a calculation means for performing a calculation in response to signals from the first and second sensors to determine the hematocrit value of the blood to be separated therefrom.

6. The apparatus according to claim 5, wherein the second sensor senses the flow of the erythrocyte fraction and the calculation means comprises means for calculating the hematocrit value according to the following formula:

$$Hk_B = \frac{V_{EK}}{V_B} \cdot K$$

wherein

Hk$_B$ = Hk of the blood
K = constant (target hematocrit)
V$_{EK}$ = erythrocyte concentrate flow
V$_B$ = blood flow.

7. The apparatus according to claim 5, wherein the second sensor senses the flow of the plasma fraction and the calculation means comprises means for calculating the hematocrit value according to the following formula:

$$Hk_B = \frac{V_B - V_{PLS}}{V_B} \cdot K$$

wherein

Hk$_B$ = Hk of the blood
K = constant (target hematocrit)
V$_B$ = blood flow
V$_{PLS}$ = plasma flow.

8. The apparatus according to claim 5, wherein the calculation means calculates the hematocrit value and the regulating means adjusts the blood flow iteratively according to an approximation process.

9. The apparatus according to claim 8, wherein the regulating means adjusts the blood flow is based on the plasma flow.

10. The apparatus according to claim 8, wherein the regulating means adjusts the blood flow based on the erythrocyte concentrate flow.

11. A process for maintaining a constant hematocrit value of the erythrocyte fraction of a blood separator, the separator having an intake line, discharge lines for outputting at least an erythrocyte fraction and a cell-poor plasma fraction and a return line for returning at least one component to a donor or patient, the process comprising the steps of:
    regulating the flow of blood supply to the separator by a pump,
    sensing hematocrit value of incoming blood at the intake line,
    separating blood into said fractions by the separator, and
    adjusting the pump in response to the hematocrit value of the incoming blood to maintain constant hematocrit value of erythrocyte fraction returned from the separator.

12. The process according to claim 11, wherein the second sensor senses erythrocyte concentrate flow and the process further comprising the step of calculating:

$$Hk_B = \frac{V_{EK}}{V_B} \cdot K$$

wherein

Hk$_B$ = Hk of the blood
K = constant (target hematocrit)
V$_{EK}$ = erythrocyte concentrate flow
V$_B$ = blood flow.

13. The process according to claim 11, wherein the separating step separates the blood using a centrifuge.

14. The process according to claim 11, further comprising the step of:
    sensing blood flow into the separator by a first sensor,
    sensing flow of a separated fraction output from the separator by a second sensor, and
    calculating, in response to outputs of the first and second sensors, the hematocrit value of the blood to be separated therefrom.

15. The process according to claim 14, wherein the second sensor senses plasma flow and the process further comprising the step of calculating:

$$Hk_B = \frac{V_B - V_{PLS}}{V_B} \cdot K$$

wherein $Hk_B$ = Hk of the blood
K = constant (target hematocrit)
$V_B$ = blood flow
$V_{PLS}$ = plasma flow.

16. The process according to claim 14, wherein the calculation step and the adjusting step of the blood flow occur iteratively according to an approximation process.

* * * * *